United States Patent
Arora et al.

(10) Patent No.: US 9,955,892 B2
(45) Date of Patent: *May 1, 2018

(54) USING INTRACARDIAC ELECTROGRAMS TO PREDICT LOCATION OF FIBROSIS AND AUTONOMIC NERVES IN THE HEART

(71) Applicant: Northwestern University, Evanston, IL (US)

(72) Inventors: Rlshi Arora, Chicago, IL (US); Jason Ng, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/836,833

(22) Filed: Aug. 26, 2015

(65) Prior Publication Data

US 2015/0366477 A1 Dec. 24, 2015

Related U.S. Application Data

(63) Continuation of application No. 13/890,112, filed on May 8, 2013, now Pat. No. 9,149,200.

(Continued)

(51) Int. Cl.
*A61B 5/046* (2006.01)
*A61B 5/04* (2006.01)
(Continued)

(52) U.S. Cl.
CPC .......... *A61B 5/046* (2013.01); *A61B 5/04012* (2013.01); *A61B 5/4887* (2013.01);
(Continued)

(58) Field of Classification Search
CPC ... A61B 5/04012; A61B 5/0402; A61B 5/046; A61B 5/4887; A61B 2018/00577;
(Continued)

(56) References Cited

U.S. PATENT DOCUMENTS 5,323,781 A * 6/1994 Ideker .................. A61B 5/0464
600/439
6,236,883 B1 * 5/2001 Ciaccio .............. A61B 5/04525
600/515

(Continued)

OTHER PUBLICATIONS

Aistrup, G.et al., "Targeted G-protein Inhibition as a Novel Approach to Decrease Vagal Atrial Fibrillation by Selective Parasympathetic Attenuation," Cardiovascular Research (2009) 83:481-492.

(Continued)

*Primary Examiner* — Christopher A Flory
(74) *Attorney, Agent, or Firm* — Klintworth & Rozenblat IP LLP

(57) ABSTRACT

A method of targeting fibrosis or autonomic nerve tissue for ablation in a subject is provided. The method includes performing at least one EGM analysis of a plurality of recorded atrial EGMs for a tissue in a region suspected of having fibrosis or autonomic nerve tissue. With regard to targeting fibrosis for ablation, the method includes determining one or more correlations of at least one AF EGM characteristic to a region having fibrosis from the plurality of recorded atrial EGMs for the tissue and determining whether the tissue contains dense fibrosis that would preclude effective ablation of the analysis region of the tissue. With regard to targeting autonomic nerve for ablation, the method includes determining whether one or more significant changes in EGM characteristics with autonomic blockade exist that would indicate the need to perform ablation of the analysis region of the tissue.

11 Claims, 9 Drawing Sheets
(4 of 9 Drawing Sheet(s) Filed in Color)

Related U.S. Application Data

(60) Provisional application No. 61/644,291, filed on May 8, 2012.

(51) Int. Cl.
*A61B 18/00* (2006.01)
*A61B 5/00* (2006.01)
*A61B 18/14* (2006.01)
*A61B 34/10* (2016.01)
*A61N 1/39* (2006.01)
*A61B 5/042* (2006.01)

(52) U.S. Cl.
CPC .............. *A61B 18/00* (2013.01); *A61B 18/14* (2013.01); *A61B 34/10* (2016.02); *A61B 5/0044* (2013.01); *A61B 5/0422* (2013.01); *A61B 5/4035* (2013.01); *A61B 5/4893* (2013.01); *A61B 2018/00351* (2013.01); *A61B 2018/00434* (2013.01); *A61B 2018/00577* (2013.01); *A61B 2018/00839* (2013.01); *A61B 2562/046* (2013.01); *A61N 1/395* (2013.01)

(58) Field of Classification Search
CPC ......... A61B 18/00; A61B 18/14; A61B 34/10; A61N 1/395
USPC .................................................. 600/510, 518
See application file for complete search history.

(56) References Cited

U.S. PATENT DOCUMENTS

| | | | | |
|---|---|---|---|---|
| 6,292,695 | B1* | 9/2001 | Webster, Jr. ......... | A61N 1/0563 607/113 |
| 7,787,946 | B2* | 8/2010 | Stahmann ............ | A61B 5/0031 607/3 |
| 2004/0082870 | A1* | 4/2004 | Rudy ................. | A61B 5/04085 600/509 |
| 2005/0112759 | A1* | 5/2005 | Radisic ............... | C12N 5/0658 435/366 |
| 2005/0197587 | A1* | 9/2005 | Rudy ................. | A61B 5/04085 600/509 |
| 2005/0288599 | A1* | 12/2005 | MacAdam ............ | A61B 5/046 600/509 |
| 2006/0247701 | A1* | 11/2006 | Zacouto ................. | C12N 13/00 607/9 |
| 2008/0161258 | A1* | 7/2008 | Henning ............ | A61K 38/1709 514/44 R |
| 2008/0208271 | A1* | 8/2008 | Sih .......................... | A61N 1/05 607/5 |
| 2009/0204113 | A1* | 8/2009 | MacAdam ............ | A61B 5/046 606/41 |
| 2009/0253974 | A1* | 10/2009 | Rahme ............... | A61B 18/1492 600/372 |
| 2009/0299424 | A1* | 12/2009 | Narayan ............... | A61B 5/0402 607/9 |
| 2010/0160765 | A1* | 6/2010 | Marrouche ........... | G06T 7/0012 600/410 |
| 2010/0160768 | A1* | 6/2010 | Marrouche ............ | A61B 6/503 600/420 |
| 2010/0189701 | A1* | 7/2010 | Cohen ................. | A01K 67/0271 424/93.21 |
| 2010/0190731 | A1* | 7/2010 | Olgin .................... | A61K 31/00 514/25 |
| 2010/0298694 | A1* | 11/2010 | Marrouche .......... | A61B 5/7275 600/420 |
| 2011/0137362 | A1* | 6/2011 | Foreman ............ | A61N 1/36114 607/14 |
| 2011/0218515 | A1* | 9/2011 | Olgin .................... | A61K 31/00 604/500 |
| 2011/0230775 | A1* | 9/2011 | Barley ............... | A61B 5/02007 600/508 |
| 2011/0245756 | A1* | 10/2011 | Arora ................... | A61N 1/0412 604/20 |
| 2011/0281853 | A1* | 11/2011 | Arora ................... | A61K 31/135 514/220 |
| 2012/0078129 | A1* | 3/2012 | Bailin .................... | A61B 5/042 600/508 |
| 2012/0109231 | A1* | 5/2012 | Sharma ............... | G06F 19/3406 607/3 |
| 2012/0157822 | A1* | 6/2012 | van Dam ............. | A61B 5/0402 600/411 |
| 2012/0303080 | A1* | 11/2012 | Ben-David .......... | A61N 1/0556 607/14 |
| 2013/0096394 | A1* | 4/2013 | Gupta ................. | A61B 5/04012 600/301 |
| 2013/0131746 | A1* | 5/2013 | Simon .................. | A61N 1/3625 607/9 |
| 2013/0303879 | A1* | 11/2013 | MacAdam ............. | A61B 5/046 600/410 |
| 2014/0023256 | A1* | 1/2014 | Nazarian .............. | A61B 5/7203 382/131 |
| 2014/0037545 | A1 | 2/2014 | Arora | |
| 2015/0088019 | A1* | 3/2015 | MacAdam ............ | A61B 5/046 600/518 |

OTHER PUBLICATIONS

Arora, R., et al., "Unique Autonomic Profile of the Pulmonary Veins and Posterior Left Atrium," Journal of American College of Cardiology (2007) 49: 1340-1348.

Burashnikov, A., et al., "Transmembrane Action Potential Heterogeneity in the Canine Isolated Arterially Perfused Right Atrium: Effect of IKr and IKur/Ito Block," Am. J. Heart Circ. Physiol. (2004) 286: H2393-H2400.

Chen, P., et al., "Autonomic Nerve Activity and Atrial Fibrillation," Heart Rhythm (2007) 4:S61-S64.

Ciaccio, E., et al., "Different Characteristics of Complex Fractionated Atrial Electrograms in Acute Paroxysmal Versus Long-standing Persistent Atrial Fibrillation," Heart Rhythm (2010) 7:1207-1215.

Ciaccio, E. et al., "Differences in Repeating Patterns of Complex Fractionated Left Atrial Electrograms in Longstanding Persistent Atrial Fibrillation as Compared with Paroxysmal Atrial Fibrillation," Circ. Arrhythm. Electrophysiol. (2011) 4:470-477.

Deyell, M.W. et al., "How we ablate ventricular tachycardia in non-ischemic, left ventricular cardiomyopathy", The Journal of Innovations in Cardiac Rhythm Management, 2 (2011), 558-565.

Everett, T. et al., "Assessment of Global Atrial Fibrillation Organization to Optimize Timing of Atrial Defibrillation," Circulation (2001) 103:2857-2861.

Everett, T. et al., "Frequency Domain Algorithm for Quantifying Atrial Fibrillation Organization to Increase Defibrillation Efficacy," IEEE Transactions on Biomedical Engineering (2001) 48:969-978.

Gardner, P. et al., "Electrophysiologic and Anatomic Basis for Fractionated Electrograms Recorded from Healed Myocardial Infarcts," Circulation (1985) 72:596-611.

Habel, N., et al., "The Impact of Pharmacologic Sympathetic and Parasympathetic Blockade on Atrial Electrogram Characteristics in Patients with Atrial Fibrillation," Pace (2011) 34:1460-1467.

Hayward, R., et al., "Pulmonary Vein Isolation with Complex Fractionated Atrial Electrogram Ablation for Paroxysmal and Nonparoxysmal Atrial Fibrillation: A Meta-analysis," Heart Rhythm (2011) 8:994-1000.

International Search Report, International Application No. PCT/US2013/040162 dated Sep. 19, 2013.

Kim, Y. et al., "A Myocardial Nox2 Containing NAD(P)H Oxidase Contributes to Oxidative Stress in in Human Atrial Fibrillation," Circ. Res. (2005) 97:629-636.

Li, D., et al., "Promotion of Atrial Fibrillation by Heart Failure in Dogs: Atrial Remodeling of a Different Sort," Circulation (1999) 100:87-95 D.

Katritsis, D. et al., "Complex Fractionated Atrial Electrograms at Anatomic Sites of Ganglionated Plexi in Atrial Fibrillation," Europace (2009) 11 :308-315.

(56) References Cited

OTHER PUBLICATIONS

Knecht, S., et al., "Impact of Pharmacological Autonomic Blockade on Complex Fractionated Atrial Electrograms," J. Cardiovasc Electrophysiol (2010) 21 :766-772.

Lin, J. et al., "Autonomic Mechanism to Explain Complex Fractionated Atrial Electrograms (CFAE)," J. Cardiovasc. Electrophysiol. (2007) 18: 1197-1205.

Lin, Y, et al. "Consistency of Complex Fractionated Atrial Electrograms During Atrial Fibrillation," Heart Ryhthm (2008) 5:406-412.

Liu, X. et al., "Decreased Connexin 43 and Increased Fibrosis in Atrial Regions Susceptible to Complex Fractionated Atrial Electrograms," Cardiology (2009) 114:22-29.

Nademanee, K., "A New Approach for Catheter Ablation of Atrial Fibrillation: Mapping of the Electrophysiologic Substrate," Journal of the American College of Cardiology (2004) 43:2044-2053.

Nademanee, K., et al., "Catheter Ablation of Atrial Fibrillation Guided by Complex Fractionated Atrial Electrogram Mapping of Atrial Fibrillation Substrate," Journal of Cardiology (2010) 55:1-12.

Na Itel, S., et al., "Atrial Remodeling and Atrial Fibrillation: Mechanisms and Implications", Circ. Arrhythm. Electrophysiol. (2008) 1: 62-73.

Nattel, S., "From Guidelines to Bench: Implications of Unresolved Clinical Issues for Basic Investigations of Atrial Fibrillation Mechanisms," Canadian Journal of Cardiology (2011) 27:19-26.

Ng, J., "Effect of Electrogram Characteristics on the Relationship of Dominant Frequency to Atrial Activation Rate in Atrial Fibrillation," Heart Rhythm (2006) 3:1295-1305.

Ng, J. et al., "Technical Considerations for Dominant Frequency Analysis," Journal of Cardiovascular Electrophysiol. (2007) 18:757-764.

Ng, J. et al., "Measuring the Complexity of Atrial Fibrillation Electrograms," Journal of Cardiovascular Electrophysiology (2010) 21 :649-655.

Ng, J., et al., "Autonomic Remodeling in the Left Atrium and Pulmonary Veins in Heart Failure: Creation of a Dynamic Substrate for Atrial Fibrillation," Circ. Arrhythm. Electrophysiol. Jun. 4, 2011(3):388-396.

Ogawa, M., et al., "Left Stellate Ganglion and Vagal Nerve Activity and Cardiac Arrhythmias in Ambulatory Dogs with Pacing-Induced Congestive Heart Failure," Journal of the American College of Cardiology (2007) 50:335-343.

Ogawa, M., et al, "Cryoablation of Stellate Ganglia and Atrial Arrhythmia in Ambulatory Dogs with Pacing-Induced Heart Failure," Heart Rhythm (2009) 6:1772-1779.

Oh, S., et al., "Complex Fractionated Electrograms and AF Nests in Vagally Mediated Atrial Fibrillation," PACE (2010) 33:1497-1503.

Schotten, U. et al., "Pathophysiological Mechanisms of Atrial Fibrillation: A Translational Appraisal," Physiol Rev. (2011) 91:265-325.

Solheim, E. et al., "Characteristics and Distribution of Complex Fractionated Atrial Electrograms in Patients with Paroxysmal and Persistent Atrial Fibrillation," J Interv Card Electrophysiol. (2010) 28:87-93.

Stambler, B. et al., "Characterization of Sustained Atrial Tachycardia in Dogs with Rapid Ventricular Pacing-Induced Heart Failure," Journal of Cardiovascular Electrophysiology (2003) 14:499-507.

Verma, A., "The Techniques for Catheter Ablation of Paroxysmal and Persistent Atrial Fibrillation: A Systematic Review,". Current Opinion in Cardiology (2011) 26:17-24.

Written Opinion of the International Searching Authority, International Application No. PCT/US2013/040162 dated Sep. 19, 2013.

Xi, Q., "Relationship Between Pattern of Occurrence of Atrial Fibrillation and Surface Electrocardiographic Fibrillatory Wave Characteristics," Heart Rhythm (2004) 1 :656-663.

Yamabe, H. et al., "Mechanisms of the Maintenance of Atrial Fibrillation: Role of the Complex Fractionated Atrial Electrogram Assessed by Noncontact Mapping," Heart Rhythm (2009) 6:1120-1128.

* cited by examiner

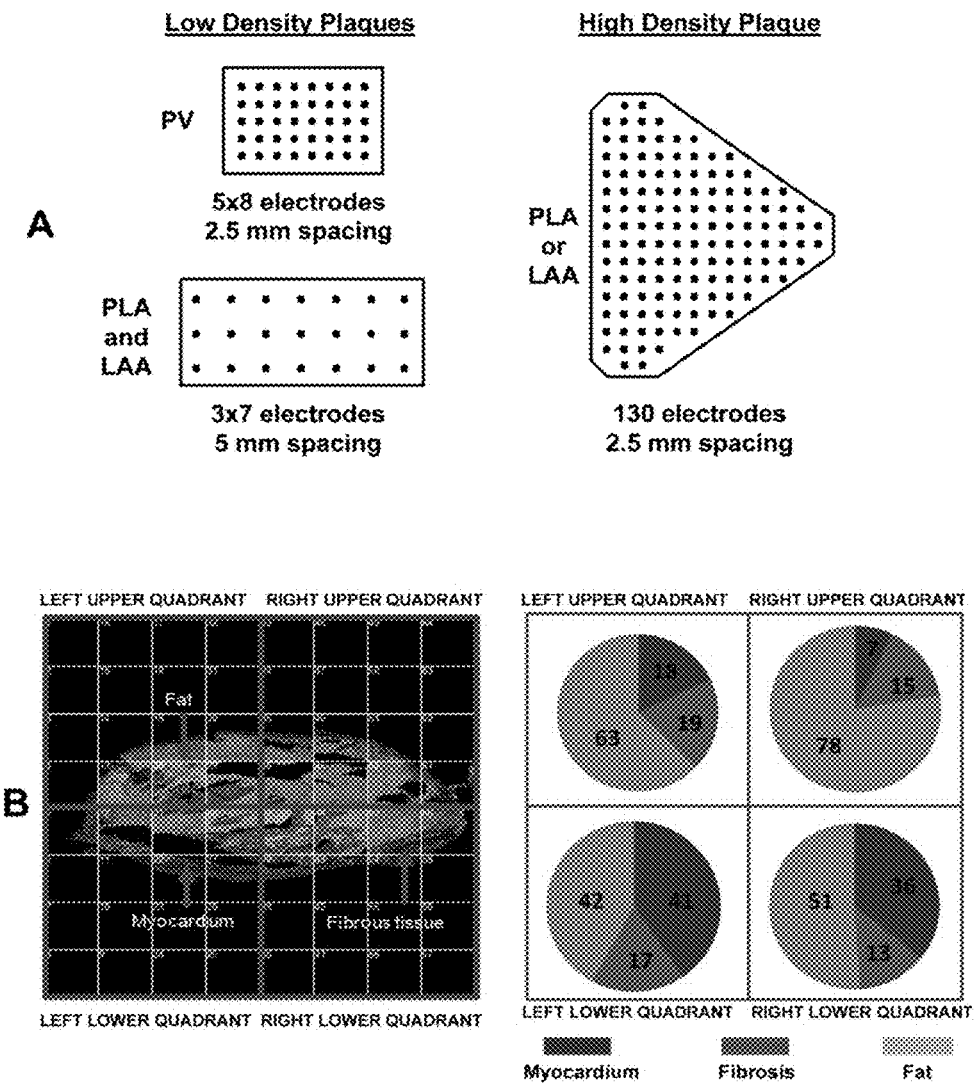
FIG. 3 (A-B)

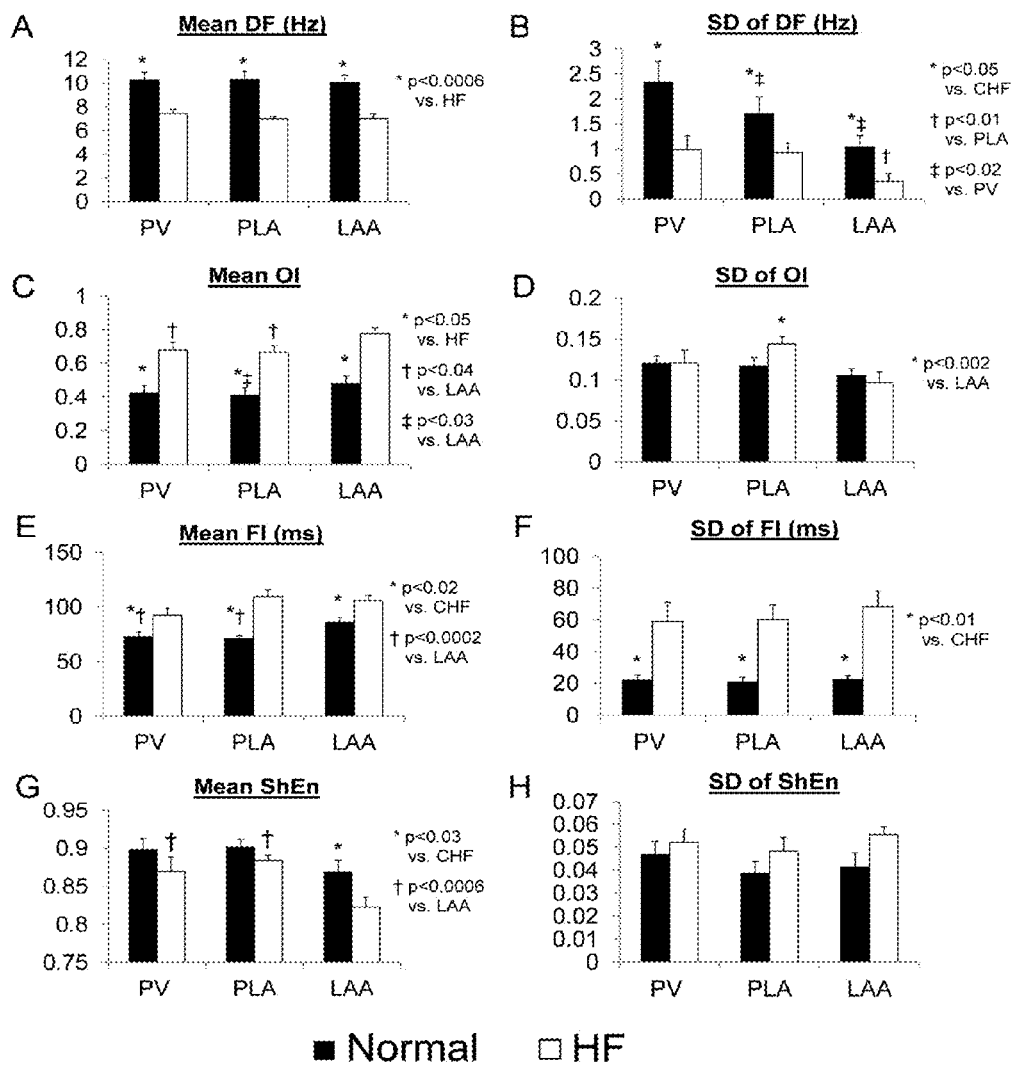
FIG. 4 (A-H)

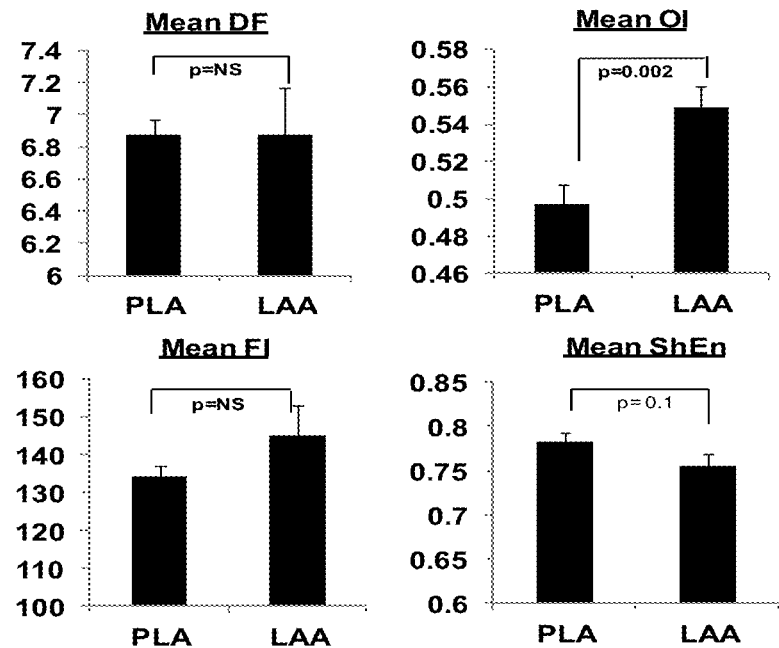
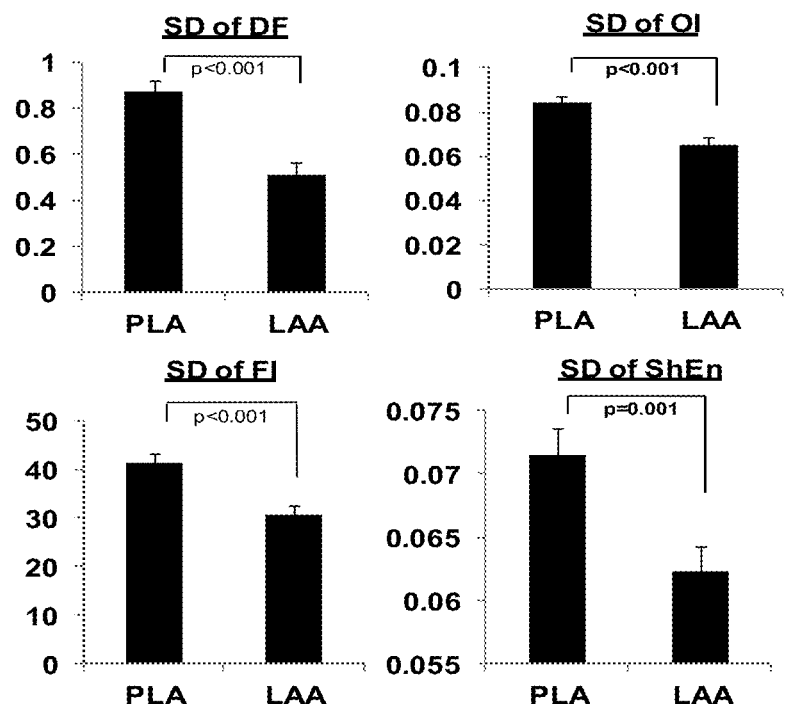
FIG. 5 (A-B)

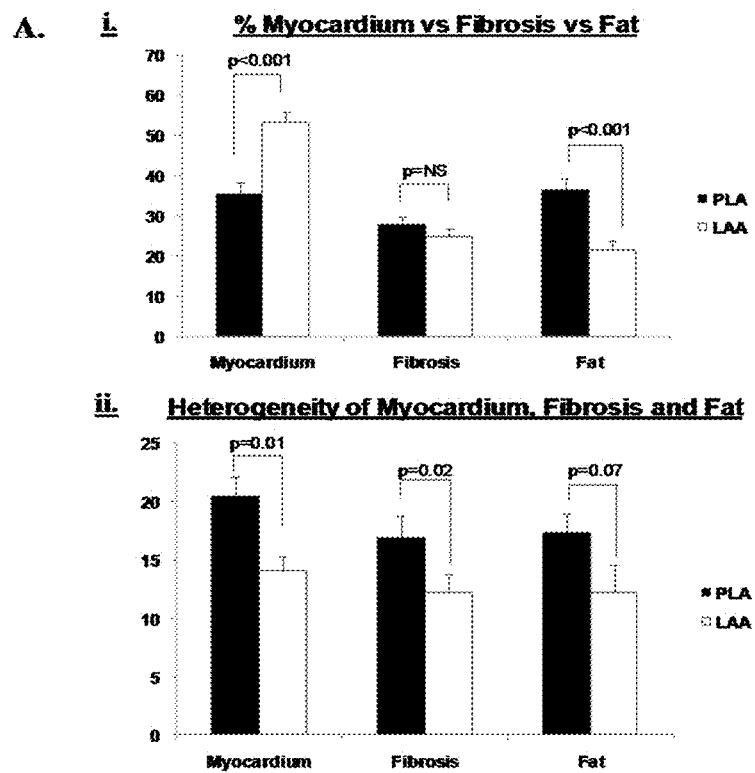
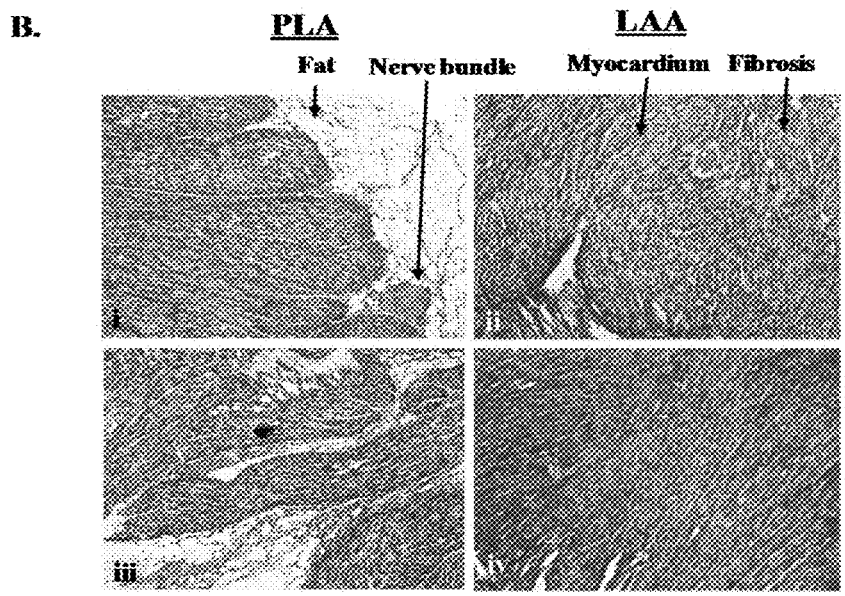
FIG. 6 (A-B)

A.
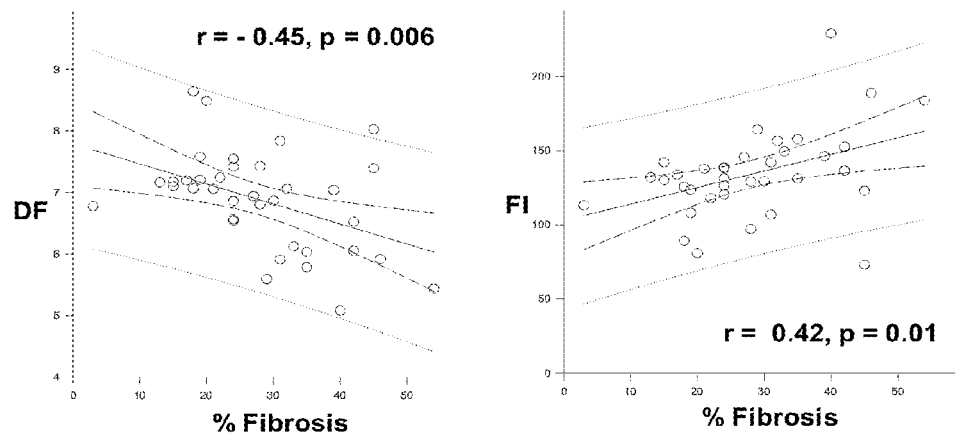
B.
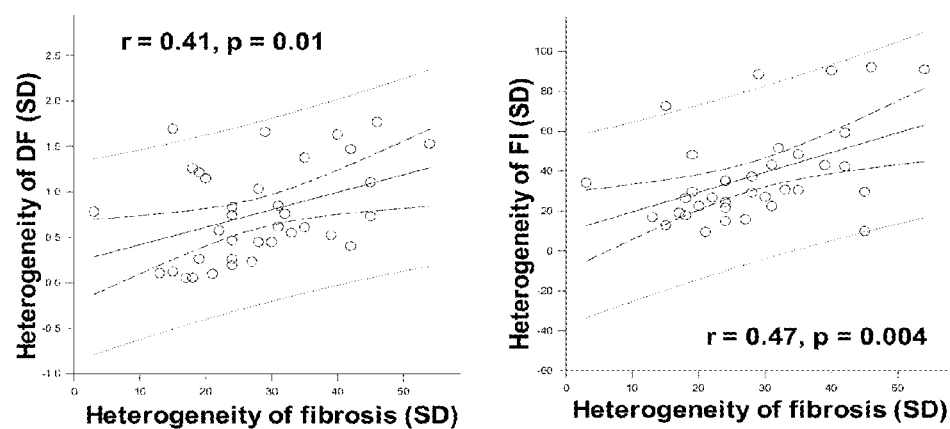
C.
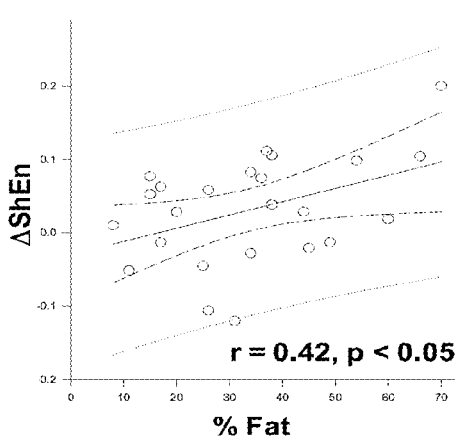
FIG. 7 (A-C)

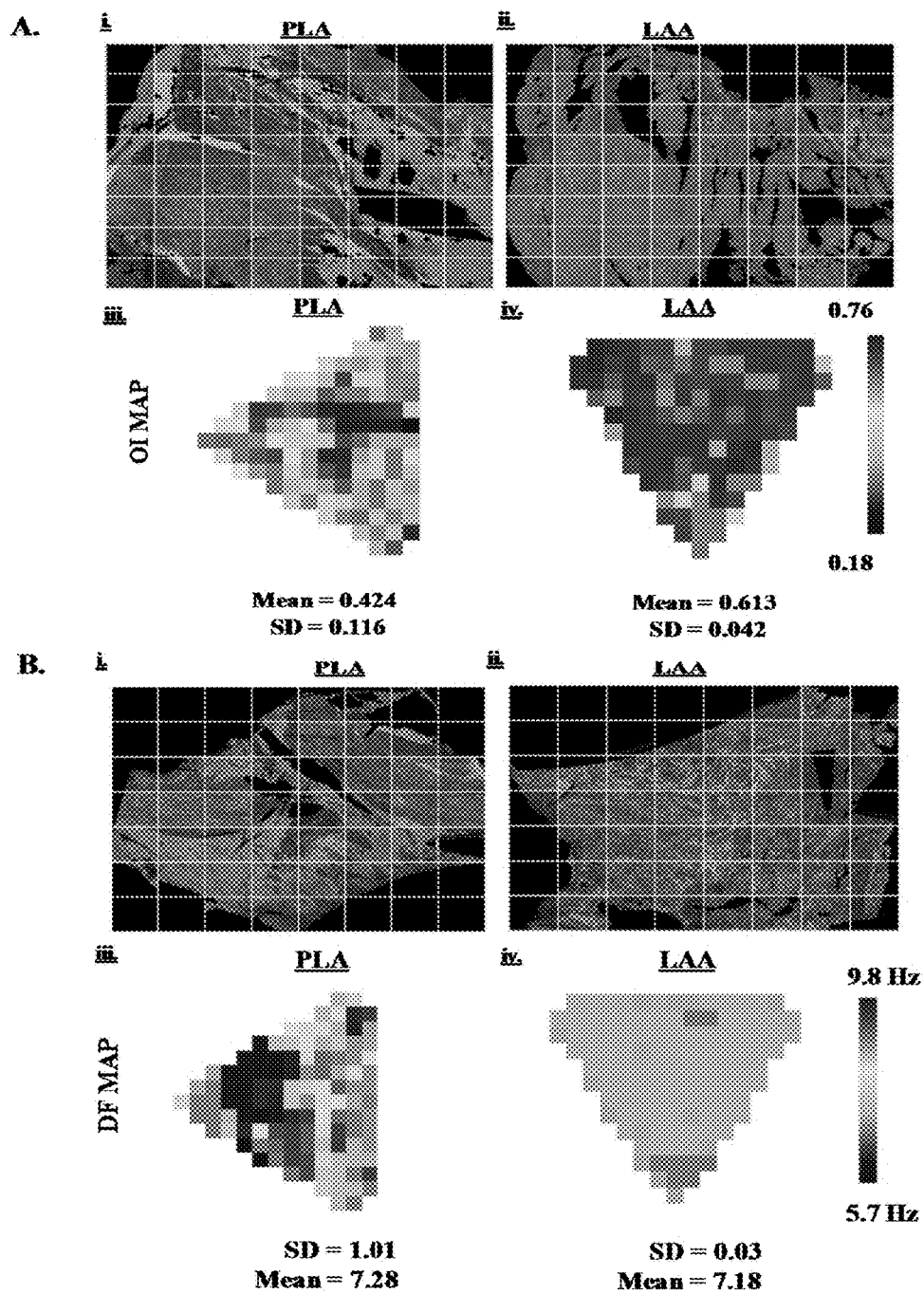
FIG. 8 (A-B)

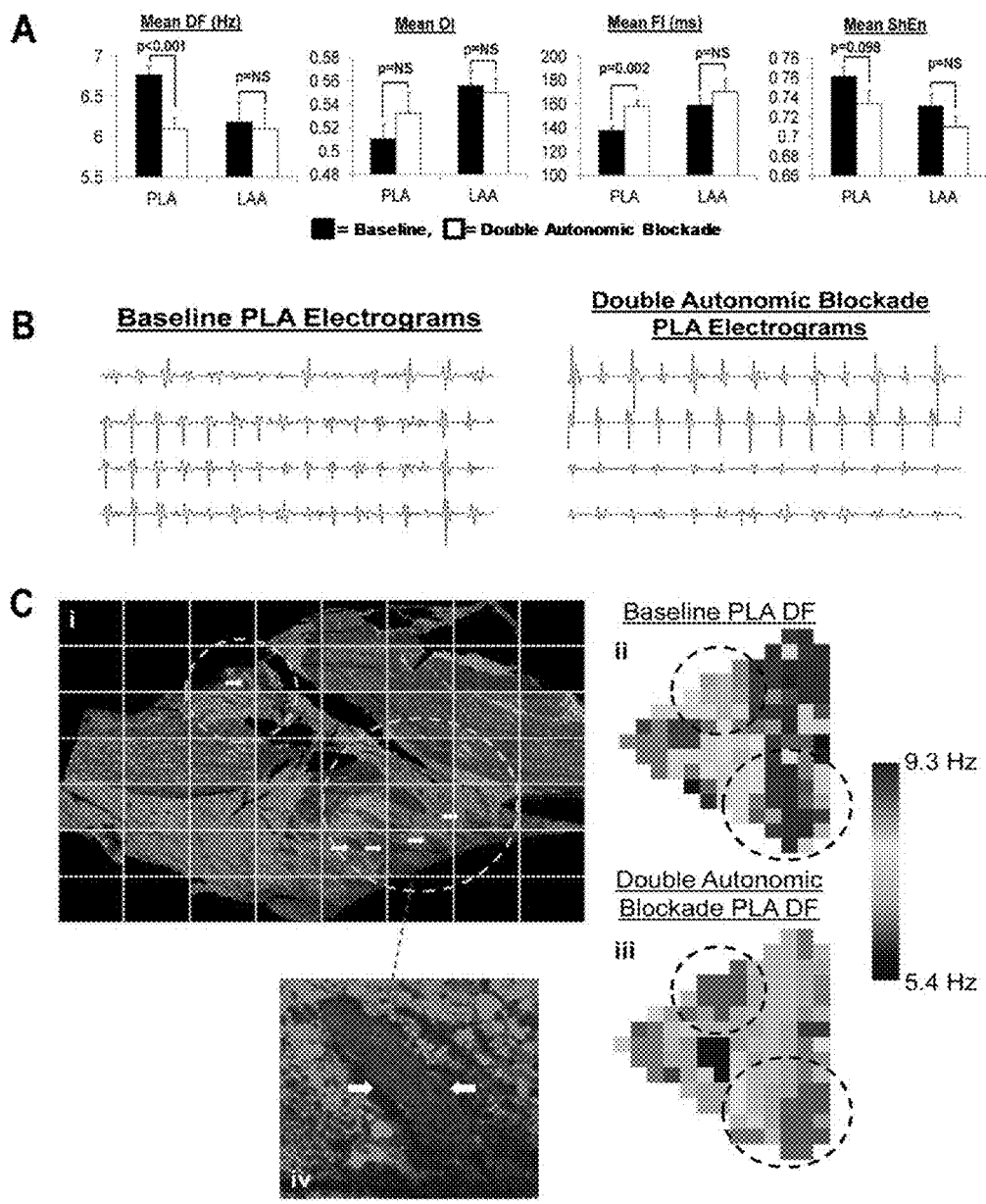
FIG. 9(A-C)

US 9,955,892 B2

USING INTRACARDIAC ELECTROGRAMS TO PREDICT LOCATION OF FIBROSIS AND AUTONOMIC NERVES IN THE HEART

CROSS-REFERENCE TO RELATED APPLICATIONS

The present application is a continuation of U.S. patent application Ser. No. 13/890,112, filed May 8, 2013, and entitled "USING INTRACARDIAC ELECTROGRAMS TO PREDICT LOCATION OF FIBROSIS AND AUTONOMIC NERVES IN THE HEART," which claims the benefit of priority under 35 U.S.C. 119 to U.S. provisional application No. 61/644,291 filed May 8, 2012, and entitled "USING INTRACARDIAC ELECTROGRAMS TO PREDICT LOCATION OF FIBROSIS AND AUTONOMIC NERVES IN THE HEART," the contents of which are hereby incorporated by reference in their entirety.

STATEMENT REGARDING FEDERALLY SPONSORED RESEARCH OR DEVELOPMENT

This invention was made with government support under ROIHL093490 awarded by the National Institutes of Health. The government has certain rights in the invention.

FIELD OF THE INVENTION

The invention relates generally to methods of detecting fibrosis in cardiac tissue and treatment modalities for ablating fibrotic tissue in cardiac disease.

BACKGROUND

Atrial fibrillation (AF) is a complex arrhythmia with a variety of underlying molecular and structural mechanisms contributing to a vulnerable AF substrate. The complexity of AF substrate seems to be reflected in the characteristics of AF electrograms (EGMs), with AF EGM morphology in paroxysmal AF being different than in more persistent AF. However, the precise structural and functional mechanisms that lead to the formation of AF EGMs have not been well elucidated. The need for a better understanding of the mechanisms underlying AF EGM formation is heightened by several recent descriptions of regions of high-frequency activity during AF called complex fractionated atrial EGMs (CFAEs). Several recent reports suggest that ablation of CFAEs seems to increase AF ablation success.

In the setting of structural heart disease, specifically heart failure (HF), a variety of mechanisms (for example, changes in ion-channel expression and gap junction distribution, inflammation, oxidative stress, and a variety of structural changes) are thought to contribute to the creation of a vulnerable AF substrate. Of the structural changes that occur in the HF atrium, fibrosis is considered to be especially important in creating conditions conducive to the genesis and maintenance of AF. In more structurally normal hearts, other mechanisms (for example, heightened autonomic activity) are thought to play a more dominant role in the genesis of AF.

Yet fundamental information remains lacking about how best to detect fibrotic tissues in AF EGM and how that information can be used to perform directed ablation of fibrotic tissue to improve AF ablation success.

BRIEF SUMMARY

In a first respect, a method of targeting fibrosis for ablation in a subject is disclosed. The method includes the following steps. First, the method performs at least one EGM analysis of a plurality of recorded atrial EGMs for a tissue in a region suspected of having fibrosis. Second, the method determines one or more correlations of at least one AF EGM characteristic to a region having fibrosis from the plurality of recorded atrial EGMs for the tissue. Third, the method determines a first outcome of executing step (b) and a second outcome of executing step (b) for the tissue based upon the one or more correlations of at least one AF EGM characteristic to a region having fibrosis. The first outcome triggers a first decision to avoid ablation of the analysis region and the second outcome triggers a second decision to perform ablation of the analysis region of the tissue.

In a second respect, a method of targeting autonomic nerve for ablation in a subject is disclosed. First, method performs at least one EGM analysis of a plurality of recorded atrial EGMs for a tissue in a region suspected of having autonomic nerve tissue. Second, the method assesses the plurality of EGMs before or after autonomic blockade. The method determines a first outcome of executing step (b) and a second outcome of executing step (b) for a region based upon the one or more significant changes in EGM characteristics with autonomic blockade. The first outcome triggers a first decision to avoid ablation of the analysis region and the second outcome triggers a second decision to perform ablation of the analysis region of the tissue.

In a third respect, a computer program product is provided that includes a computer readable medium having computer readable program code for targeting fibrosis or autonomic nerve for ablation in a subject, wherein targeting fibrosis or autonomic nerve includes: (a) performing at least one EGM analysis of a plurality of recorded atrial EGMs for a tissue; and (b) executing at least one of the following sets of instructions. With respect to targeting fibrosis for ablation, the instructions include (i) determining one or more correlations of at least one AF EGM characteristic to a region having fibrosis from the plurality of recorded atrial EGMs for the tissue; and (ii) determining a first outcome of executing step (b) and a second outcome of executing step (i) for the tissue based upon the one or more correlations of at least one AF EGM characteristic to a region having fibrosis. In accordance with this set of instructions, the first outcome triggers a first decision to avoid ablation of the analysis region and the second outcome triggers a second decision to perform ablation of the analysis region of the tissue. In the alternative, with respect to targeting autonomic nerve for ablation, the instructions include: (i) assessing the plurality of EGMs before or after autonomic blockade; and (ii) determining a first outcome of executing step (i) and a second outcome of executing step (i) for a region based upon the one or more significant changes in EGM characteristics with autonomic blockade. In accordance with this set of instructions, the first outcome triggers a first decision to avoid ablation of the analysis region and the second outcome triggers a second decision to perform ablation of the analysis region of the tissue.

In a fourth respect, a kit is provided. The kit includes: (a) a computer program product as disclosed in the third respect; and (b) instructions.

These and other features, objects and advantages of the present invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The features, objects and advantages other than those set forth above will become more readily apparent when consideration is given to the detailed description below. Such detailed description makes reference to the following drawings.

FIG. 3A depicts density and inter-electrode spacing of the low- and high-density plaques used for atrial fibrillation (AF) electrogram (EGM) mapping.

FIG. 3B illustrates an exemplary EGM map of the entire posterior left atrium (PLA) section, composed of several individual photo-micrographs at 4× magnification (left) and how the PLA section on the left was divided into 4 quadrants; for each quadrant, tissue composition (that is, % fat vs myocardium vs fibrosis was assessed; see sub-panel on the right for tissue composition for each quadrant). LAA indicates left atrial appendage; PV, pulmonary vein (right).

FIG. 4A depicts graphical data comparisons of mean dominant frequency (DF) in normal (black bars) vs heart failure (HF) (white bars) atria of each atrial fibrillation (AF) measure. Comparisons were made for mean and SD of each atrial fibrillation (AF) measure. Comparisons were made for the posterior left atrium (PLA), pulmonary vein (PV), and left atrial appendage (LAA). CHF indicates congestive heart failure. Symbols above the bar graphs indicate statistical significance of data.

FIG. 4B depicts graphical data comparisons of standard deviation (SD) dominant frequency (DF) in normal (black bars) vs heart failure (HF) (white bars) atria of each atrial fibrillation (AF) measure. Comparisons were made for mean and SD of each atrial fibrillation (AF) measure. Comparisons were made for the PLA, PV and LAA. Abbreviations are as set forth in FIG. 4A.

FIG. 4C depicts graphical data comparisons of mean organization index (OI) in normal (black bars) vs heart failure (HF) (white bars) atria of each atrial fibrillation (AF) measure. Comparisons were made for mean and SD of each atrial fibrillation (AF) measure. Comparisons were made for the PLA, PV and LAA. Abbreviations are as set forth in FIG. 4A.

FIG. 4D depicts graphical data comparisons of standard deviation (SD) organization index (OI) in normal (black bars) vs heart failure (HF) (white bars) atria of each atrial fibrillation (AF) measure. Comparisons were made for the PLA, PV and LAA. Abbreviations are as set forth in FIG. 4A.

FIG. 4E depicts graphical data comparisons of mean fractionation interval (FI) in normal (black bars) vs heart failure (HF) (white bars) atria of each atrial fibrillation (AF) measure. Comparisons were made for mean and SD of each atrial fibrillation (AF) measure. Comparisons were made for the PLA, PV and LAA. Abbreviations are as set forth in FIG. 4A.

FIG. 4F depicts graphical data comparisons of standard deviation (SD) fractionation interval (FI) in normal (black bars) vs heart failure (HF) (white bars) atria of each atrial fibrillation (AF) measure. Comparisons were made for mean and SD of each atrial fibrillation (AF) measure. Comparisons were made for the PLA, PV and LAA. Abbreviations are as set forth in FIG. 4A.

FIG. 4G depicts graphical data comparisons of mean Shannon entropy (ShEn) in normal (black bars) vs heart failure (HF) (white bars) atria of each atrial fibrillation (AF) measure. Comparisons were made for mean and SD of each atrial fibrillation (AF) measure. Comparisons were made for the PLA, PV and LAA. Abbreviations are as set forth in FIG. 4A.

FIG. 4H depicts graphical data comparisons of standard deviation (SD) Shannon entropy (ShEn) in normal (black bars) vs heart failure (HF) (white bars) atria of each atrial fibrillation (AF) measure. Comparisons were made for mean and SD of each atrial fibrillation (AF) measure. Comparisons were made for the PLA, PV and LAA. Abbreviations are as set forth in FIG. 4A.

FIG. 5A depicts graphical data comparisons of dominant frequency (DF), organization index (OI), fractionation interval (FI) and Shannon entropy (ShEn) in the heart failure (HF) posterior left atrium (PLA) and left atrial appendage (LAA). The statistics are indicated above the bar graphs in terms of p value. NS, not significant.

FIG. 5B depicts graphical data comparisons of heterogeneity (SD) of DF, OI, FI and ShEn in the HF PLA and LAA. Abbreviations are as set forth in FIG. 5A.

FIG. 6A depicts graphical comparisons of the relative percentages of fat, fibrosis, and myocardium in the posterior left atrium (PLA) vs left atrial appendage (LAA) in heart failure (HF) dogs are indicated (subpanel i.) and the heterogeneity of fat, fibrosis, and myocardium in the PLA and LAA of HF dogs (subpanel ii.). PLA, solid black bars; LLA, solid white bars. The statistics are indicated above the bar graphs in terms of p value. NS, not significant.

FIG. 6B illustrates histological comparisons in subpanels i (upper left)-iv (lower right), wherein the individual sections (magnification ×4) from the PLA (subpanels i and iii) and LAA (subpanels ii and iv), respectively, highlighting that (1) there is significantly more fat in the PLA than the LAA and (2) fibrosis, fat, and myocardium are all more heterogeneously distributed in the PLA than the LAA. In addition, subpanel (i) demonstrates a typical nerve trunk in the PLA.

FIG. 7A subpanels show the correlation between % fibrosis in the posterior left atrium (PLA) and dominant frequency (DF) and fractionation interval (FI), respectively ((left and right, respectively)). The statistics are indicated as insets in terms of r and p values.

FIG. 7B subpanels show the correlation between heterogeneity of fibrosis and heterogeneity of DF and FI (left and right subpanels, respectively). Abbreviations are as set forth in FIG. 7A.

FIG. 7C shows the correlation between change in Shannon entropy (ΔShEn) with autonomic blockade and % fat in the PLA. Abbreviations are as set forth in FIG. 7A.

FIG. 8A illustrates an exemplary embodiment of a posterior left atrium (PLA; subpanel i.) and left atrial appendage (LAA) section (subpanel ii.) from 1 animal. Subpanels iii. and iv. show the corresponding organization index (OI) of the atrial fibrillation (AF) signals recorded for each of these regions, respectively. The statistics are indicated below each panel in terms of mean and standard deviation (SD) values.

FIG. 8B illustrates an exemplary embodiment of a PLA (subpanel i.) and LAA section (subpanel ii.) from 1 animal. Subpanels iii. and iv. show the corresponding dominant frequency (DF) of the AF signals recorded for each of these regions, respectively. Abbreviations are as set forth in FIG. 8A.

FIG. 9A depicts graphical representation of the effects of autonomic blockade in the posterior left atrium (PLA) and left atrial appendage (LAA) on dominant frequency (DF), organization index (OI), fractionation interval (FI), and Shannon entropy (ShEn). The baseline data are indicated in solid black bars and the double autonomic blockade data is illustrated in solid white bars. The statistics are indicated above the bar graphs in terms of p value. NS, not significant.

FIG. 9B illustrates exemplary embodiments of PLA electrograms (EGMs) before and after double autonomic blockade.

FIG. 9C illustrates an exemplary embodiment of the entire PLA section being mapped (subpanel i.). The circles highlight areas containing several large nerve trunks, indicated by white arrows. Subpanels ii. and iii. show the DF of an atrial fibrillation (AF) episode recorded at baseline and in the presence of double autonomic blockade, respectively. As shown, autonomic blockade resulted in lower DFs in both the upper circle ($\approx$8-6 Hz) and in the lower circle ($\approx$9-6 Hz). Subpanel iv. shows a magnified view of a single nerve trunk seen in the lower encircled area in subpanel i. NS indicates nonsignificant.

Figure 1:
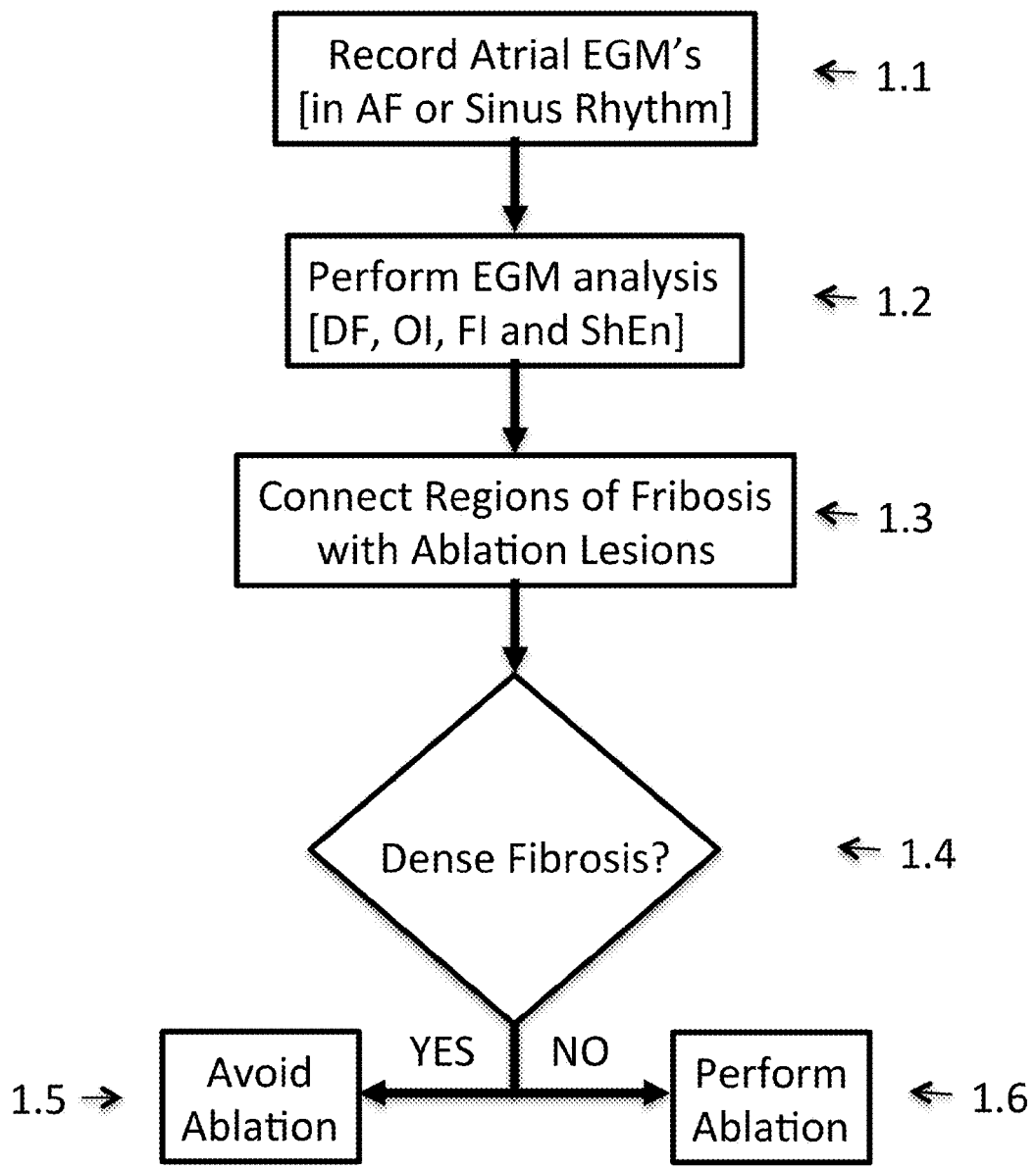
FIG. 1 depicts a flow-diagram for one preferred embodiment illustrating a treatment modality method for targeting fibrosis for treatment based upon analysis of atrial EGM's.

While the present invention is amenable to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments and claims herein for interpreting the scope of the invention.

DETAILED DESCRIPTION

The methods now will be described more fully hereinafter with reference to the accompanying drawings, in which some, but not all permutations and variations of embodiments of the invention are shown. Indeed, the invention may be embodied in many different forms and should not be construed as limited to the embodiments set forth herein. These embodiments are provided in sufficient written detail to describe and enable one skilled in the art to make and use the invention, along with disclosure of the best mode for practicing the invention, as defined by the claims and equivalents thereof.

Likewise, many modifications and other embodiments of the methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

Robust clinical diagnostic algorithms and methods are disclosed that enable use of Atrial fibrillation (AF) electrograms (EGMs) to detect specific AF mechanisms pertaining to fibrosis and autonomic nerve densities underlying AF in the context of congestive heart failure (HF). The algorithms and methods of their use derive from novel systematic comparison of tissue structure and the characteristics of overlying AF EGMs. The generated AF EGMs can be used to detect regions of dense fibrosis and high autonomic nerve density in the HF atrium. The decision end-point for the algorithms corresponds to whether specific sites should be subject to ablation therapy. The resolution of the AF EGM's, when coupled to the application of the algorithms enable increased success in performing highly precise substrate-guided ablation for HF.

Contribution of Fibrosis to AF EGMs

The correlation between AF EGM characteristics and the underlying quantity and distribution of fibrosis was systematically assessed. Using a variety of time and frequency domain measures, the signal characteristics of AF EGMs in the setting of HF (where fibrosis is known to be a key contributor to the genesis and maintenance of AF) and compared these with AF EGMs in normal hearts (where AF was induced by vagal stimulation) were examined. The relationship between the characteristics of AF EGMs in HF and the underlying distribution of myocardium, fibrosis, fat, and autonomic ganglia in the failing left atrium was also systematically assessed.

Though the details are presented in the Examples, the findings can be summarized as follows:

(1) AF EGM measures are significantly different in AF in the normal versus the HF atrium, with AF being slower (lower DF), more organized (higher OI), and having a higher FI in the setting of HF;

(2) there are significant regional differences in AF signal content in HF, with AF being less organized (lower OI) in the PLA than in the LAA; moreover, all EGM measures are significantly more spatially heterogeneous in the PLA than in the LAA;

(3) there is a significantly greater amount of fat in the PLA compared with the LAA, with the fat being richly innervated with large nerve trunks; moreover, fibrofatty tissue is more heterogeneously distributed in the PLA than in the LAA;

(4) AF signal content in the HF atrium correlates with the total amount of fibrosis, with increasing fibrosis correlating with slowing and increased organization of AF EGMs; furthermore, heterogeneity of AF signal content in the HF atrium correlates with the heterogeneity of underlying fibrosis;

(5) autonomic blockade significantly decreases DF and increases FI (with a resulting decrease in CFAEs (that is, a type of EGM-guided ablation) in the PLA; and (6) the autonomic responsiveness of AF EGMs (that is, entropy of AF signals) is directly correlated with the amount of nerve-rich fatty tissue present in the myocardium.

AF EGMs were systematically characterized in 2 well-characterized substrates for AF: (1) in a normal heart where vagal stimulation (with resulting refractory period shortening) is the primary mechanism for AF and (2) in pacing-induced HF where fibrosis is thought to be a dominant mechanism underlying AF, with other mechanisms, such as oxidative stress and autonomic dysfunction, also contributing at least partially to AF substrate. AF EGM content was significantly different in normal versus HF atria, with EGMs in HF being significantly slower, and surprisingly, more organized and less fractionated compared with AF EGMs in normal hearts. The strong correlation between the amount and heterogeneity of fibrosis and the time and frequency domain measures of AF EGMs in HF reveals that fibrosis contributes to AF EGM characteristics. Patients with AF, worsening structural heart disease appears to contribute not only to the increasing chronicity of AF but also to AF EGM content.

EGM differences between HF and normal hearts can provide valuable insight into the patho-physiologic mechanisms underlying AF and may be of potential clinical significance in patients with AF undergoing AF ablation. It is well known that success rates of ablation procedures decrease in patients with permanent AF (compared with paroxysmal AF), at least, in part, because of the presence of structural heart disease in these patients.

The addition of EGM-guided ablation (for example, complex fractionated atrial EGM [CFAE] ablation) increases long-term success of these procedures. The increased regularity of EGMs (indicated by increased OI in HF) in the presence of slower activation rates (indicated by lower DFs and higher FIs) in HF indicates the presence of regions of underlying fibrosis. An enhanced ability to identify islands dense fibrosis (by real-time AF EGM analysis) allows for a greater precision in the placement of linear ablation lesions in the atrium.

Thus, one embodiment concerns a method of targeting fibrosis for ablation in a subject. The method includes recording an Atrial EGM from a subject (FIG. 1; 1.1). The subject is preferably a mammal; most preferably, the subject is a human. The subject is preferably a patient in need of monitoring cardiovascular disease; more preferably, the subject is a patient in need of preventative treatments for stroke or congestive heart failure, in particular, where such conditions are attributed to atrial fibrillation (AF); most preferably, the subject is a patient in need of monitoring sustained arrhythmia, such as atrial fibrillation (AF).

The Atrial EGM is preferably recorded in AF or in sinus rhythm. The recording is preferably obtained by standard procedures well known in the art.

Once obtained, an analysis of the EGM is performed using one or more analytical subroutines (FIG. 1; 1.2). Preferred analytical subroutines include at least one member selected from the group consisting of dominant frequency analysis (DF), organizational index analysis (OI), fractional interval analysis (FI) and Shannon Entropy analysis (ShEn). The analysis of the EGM can be done on-line (for example, in real-time) or off-line (for example, using previously acquired EGM data provided in a readable computer media).

The analysis of the EGM performed in accordance with one or more of the aforementioned analytical subroutines permits identification of one or more correlations of at least one AF EGM characteristic to a region having fibrosis. More preferably, one or more aforementioned analytical subroutines permits identification of one or more correlations of at least two AF EGM characteristics to a region having fibrosis. Most preferably, one or more aforementioned analytical subroutines permits identification of one or more correlations of three AF EGM characteristics to a regions having fibrosis.

Preferred correlations include one or more of the following: (i) mean DF negatively correlates with % fibrosis; heterogeneity of DF negatively correlates with heterogeneity of fibrosis; mean FI positively correlates with % fibrosis; and heterogeneity of FI positively correlates with heterogeneity of fibrosis. Preferably, two correlations are selected from the group of (a) one correlation based upon % fibrosis and (b) one correlation based upon heterogeneity of fibrosis.

Thus, determining one or more correlations of at least one AF EGM characteristic to a region having fibrosis from the plurality of recorded atrial EGMs for the tissue permits the identification of one or more correlations of an AF EGM characteristic with a region suspected of having fibrosis enables one to connect regions of fibrosis with ablation lesions (FIG. 1; 1.3).

The decision is then made to avoid ablation or perform ablation on a given AF substrate based upon whether an outcome of the analysis region suspected of having fibrosis is a dense fibrosis (FIG. 1; 1.4). If a first outcome of the analysis indicates that the region contains dense fibrosis (FIG. 1, "YES" at 1.4), then the first outcome triggers a first decision to avoid ablation of the analysis region (FIG. 1; 1.5). If a second outcome of the analysis indicates that the region contains minimal fibrosis or no fibrosis dense fibrosis (FIG. 1, "NO" at 1.4), then the second outcome triggers a second decision to perform ablation of the analysis region (FIG. 1; 1.6).

Contribution of the Autonomic Nervous System to AF EGMs

Quite unexpectedly, a decrease in DF and increase in FI in the failing PLA in the presence of autonomic blockade was clearly observed. Autonomic changes in EGM content also correlated with the underlying distribution of nerve-rich fibrofatty tissue in the PLA. These results support a role for the autonomic nervous system in contributing to AF substrate in the HF setting. Indeed, both the sympathetic and the parasympathetic nervous system contribute to AF substrate in HF. The enhanced autonomic responsiveness of AF EGMs in the PLA (compared with the LAA) supports the view where autonomic remodeling in the HF atrium, both at the structural and functional levels, is significantly more pronounced in the PLA than in the rest of the left atrium. Thus, a clear contribution of fatty tissue harboring large autonomic nerve trunks to time and frequency domain measures of EGM characteristics can provide a detailed assessment of AF EGM content in the presence of autonomic blockade to better target autonomic ganglia during ablation.

Figure 2:
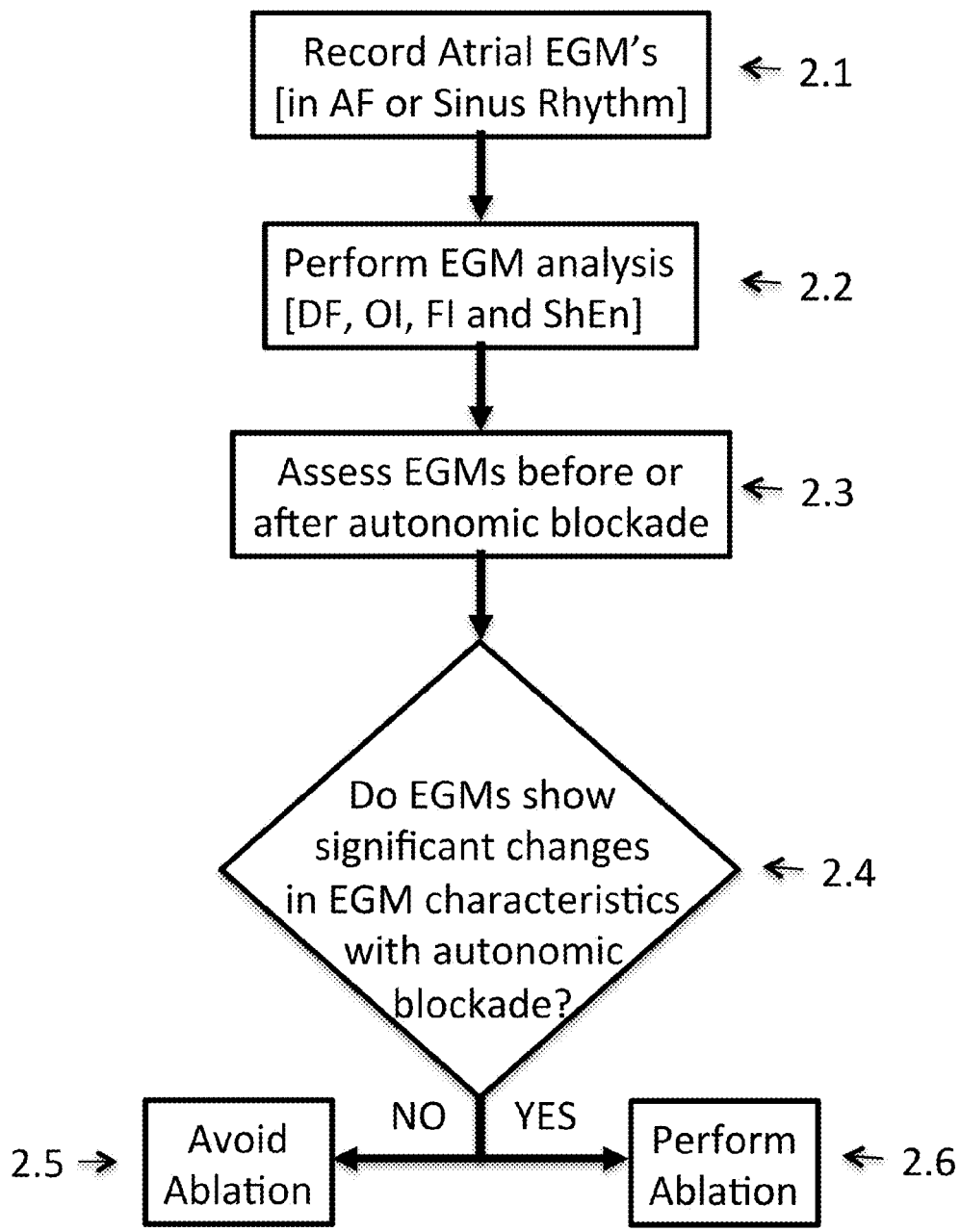
FIG. 2 depicts a flow-diagram for one preferred embodiment illustrating a treatment modality method for targeting autonomic nerve tissue for treatment based upon analysis of atrial EGM's.

Thus, another embodiment concerns a method of targeting autonomic nerve for ablation in a subject. The method includes recording an Atrial EGM from a subject (FIG. 2; 2.1). The subject is preferably a mammal; most preferably, the subject is a human. The subject is preferably a patient in need of monitoring cardiovascular disease; more preferably, the subject is a patient in need of preventative treatments for stroke or congestive heart failure, particularly where such disease conditions are attributed to autonomic nerve tissue activity; most preferably, the subject is a patient in need of monitoring sustained arrhythmia, such as atrial fibrillation (AF).

The Atrial EGM is preferably recorded in AF or in sinus rhythm. The recording is preferably obtained by standard procedures well known in the art.

Once obtained, an analysis of the EGM is performed using one or more analytical subroutines (FIG. 2; 2.2). Preferred analytical subroutines include at least one member selected from the group consisting of dominant frequency analysis (DF), organizational index analysis (OI), fractional interval analysis (FI) and Shannon Entropy analysis (ShEn). The analysis of the EGM can be done on-line (for example, in real-time) or off-line (for example, using previously acquired EGM data provided in a readable computer media).

The analysis of the EGM performed in accordance with one or more of the aforementioned analytical subroutines permits assessment of at least one AF EGM characteristic before or after autonomic blockade. Optionally, the aforementioned analytical subroutines permits assessment of at least one AF EGM characteristic of autonomic nerve before or after autonomic blockade and/or autonomic stimulation. In this optional, step autonomic stimulation can be performed using techniques well understood to the skilled artisan; preferably, however, autonomic stimulation can be performed with radio frequency or high frequency sources. Thus, the identification of at least one AF EGM characteristic having significant changes with autonomic blockade and/or with autonomic stimulation enables one to target autonomic nerve with ablation (FIG. 2; 2.3).

The decision is then made to avoid ablation or perform ablation on a given AF substrate based upon whether an outcome of the analysis region includes an EGM having a significant change in at least one EGM characteristic with autonomic blockade (and/or autonomic stimulation) (FIG. 2; 2.4). If a first outcome of the analysis indicates that the region does not contain a significant change in at least one EGM characteristic with autonomic blockade (FIG. 2, "NO" at 2.5), then the first outcome triggers a first decision to avoid ablation of the analysis region (FIG. 2; 2.5). If a second outcome of the analysis indicates that the region contains a significant change in at least one EGM characteristic with autonomic blockade (FIG. 2, "YES" at 2.4), then the second outcome triggers a second decision to perform ablation of the analysis region (FIG. 2; 2.6).

Accordingly, some embodiments according to some aspects of the present invention may be realized in hardware, software, or a combination of hardware and software. Some aspects of some embodiments of the present invention may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

Some embodiments according to some aspects of the present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

Some embodiments according to some aspects of the present invention contemplate one or more processors operatively coupled to one or more memories (for example, a non-transitory computer readable medium) in which one or more steps described herein are stored as instructions or executable code in the one or more memories and are executed by the one or more processors or are used to configure the one or more processors. Some embodiments according to some aspects of the present invention contemplate that the one or more processors and the one or more memories are part of a computer system. The computer system may be part of, for example, laboratory equipment or medical equipment.

Some embodiments according to some aspects of the present invention contemplate that the one or more processors and/or the one or more memories are part of an integrated circuit and/or an application specific integrated circuit (ASIC) and/or a single integrated circuit chip.

Some embodiments according to some aspects of the present invention contemplate using software, hardware and/or firmware.

Some embodiments according to some aspects of the present invention contemplate using a software algorithm that can be installed in commercially available EGM imaging and computer machine language-based analysis stations The software algorithm may compute, for example, correlation functions obtained from one or more of DF, OI, FI, and ShEn analyses of EGM recordings to obtain a decision whether to perform ablation therapy on a selected region. The software algorithm can be realized, for example, in Matlab, C, C++, Pascal, Java, Fortran, Perl, Basic, machine language or other programming languages. To any extent to which specific processing hardware is provided to realize the algorithm, some embodiments according to some aspects of the present invention provide for digital signal processors and/or field programmable gate array, etc. Some embodiments according to some aspects of the present invention also contemplate that a data interface with an existing EGM recording system provide raw data, which includes spectral data directly output from a recorder.

Kits are contemplated with the scope of the present disclosure. Preferred components of kits include algorithm-encoded software on a computer machine readable medium that permits execution of instructions by a machine for implementing the methods of the present invention to guide in the selection of AF substrate for substrate-guided ablation for HF. Kits can also include instructions, manuals, and on-line help sections for assisting users with implementing the executable software code.

EXAMPLES

The invention will be more fully understood upon consideration of the following non-limiting examples, which are offered for purposes of illustration, not limitation.

Example 1. Dog Protocols

Purpose-bred hound dogs (weight range, 25-35 kg) were used in the present study for both control and HF groups. This protocol conforms to the *Guide for the Care and Use of Laboratory Animals* published by the US National Institutes of Health (Publication No. 85-23, revised 1996) and was approved by the Animal Care and Use Committee of Northwestern University. Before undergoing the procedures listed below, all animals were premedicated with acepromazine (0.01-0.02 mg/kg) and were induced with propofol (3-7 mg/kg). All experiments were performed under general anesthesia (inhaled) with isoflurane (1%-3%). The adequacy of anesthesia was assessed by toe pinch and palpebral reflex Example 2. Canine HF Model In 21 dogs, HF was induced by 3 to 4 weeks of right ventricular tachypacing (240 beats per minute) by an implanted pacemaker. In 19 dogs, a transvenous pacemaker was placed via a jugular approach, under aseptic conditions. In 2 dogs, a pacemaker was placed on the ventricle via an epicardial approach (that is, via a left lateral thoracotomy). Left ventricular function was assessed during pacing by serial echocardiograms (data not shown). HF was confirmed after 3 to 4 weeks of pacing. Twenty dogs without rapid ventricular pacing were used as controls.

Example 3. Open-Chest Mapping

At the terminal study, a left lateral thoracotomy was performed. Low density and high density mapping protocols were used. The low density mapping protocol was used to compare AF EGMs from 14 HF dogs with EGMs from 20 control dogs with AF induced during vagal stimulation. With low density mapping, the posterior left atrium (PLA), left superior pulmonary vein (PV), and left atrial appendage could be mapped simultaneously. The PLA and LAA were mapped using two rectangular plaques containing 21 electrodes each (7×3 electrodes, inter-electrode distance=5 mm) from which 18 bipolar EGMs were recorded. The PV was mapped with a 40-electrode, rectangular plaque (8×5 electrodes, inter-electrode distance=2.5 mm) from which 35 bipolar EGMs were obtained. FIG. 3A shows the schematics of the plaques. The signals from the low density plaques were recorded and stored at a 977 Hz sampling rate with the GE Prucka Cardiolab system (GE Healthcare, Waukesha, Wis.).

High density mapping was performed in 8 HF dogs for detailed comparisons of EGMs with the underlying tissue structure. Mapping was performed sequentially in the PLA and LAA with a triangular plaque containing 130 electrodes (inter-electrode distance of 2.5 mm) from which 117 bipolar EGMs were recorded. The schematic is shown in FIG. 3A. The UNEMAP mapping system (Univ. of Auckland, Auckland, New Zealand) was used for recording and storing the EGMs at a 1 kHz sampling rate. Even though we did not separately map the PVs during high-density mapping (owing to the relatively large surface area of the high density plaques, it was technically challenging to cover the PVs, which have a circular and uneven surface), the high-density plaque did straddle the proximal PVs during PLA mapping. One dog underwent both low and high density mapping.

Example 4. AF Induction

AF was induced in the control animals in the presence of left cervical vagal stimulation via programmed stimulation (eight S1 beats at 400 ms followed by a single extrastimulus). For vagal stimulation, the left cervical vagus nerve was isolated and a bipolar stainless steel electrode was attached to the nerve. Vagal stimulation was performed using a Grass S44G stimulator (Astromed, West Warwick, R.I.) with a 5-10 V amplitude, a 20 Hz stimulation rate, and a 5 ms pulse width; an adequate vagal response was adjudged by: 1) sinus node slowing by at least 25% or 2) PR prolongation by more than 25% or 2:1 AV block. AF was induced in the HF dogs with burst pacing under baseline conditions using cycle lengths of 180 ms to 110 ms with 10 ms decrements for 10 seconds for each cycle length. Current was set at four times threshold for capture. In 6 of the 8 HF dogs that underwent high density mapping, AF was also induced in the presence of double autonomic blockade (0.2 mg/kg propranolol and 0.04 mg/kg atropine), in order to test the hypothesis that autonomic nerves in the ganglion-rich fibrofatty tissue also affect EGM characteristics. Ten seconds of AF in the middle of a sustained episode were recorded when high density mapping was performed, whereas the entire AF episode beginning at AF initiation was recorded when low density mapping was performed.

Example 5. Histology

The histologic analysis described below (for example, comparison of tissue make-up between PLA and LAA) and EGM-tissue analysis was only performed for HF atria, as these atria are known to harbor significant fibrosis. Normal atria on the other hand are not known to have significant fibrosis. In examples of histology from the PLA and LAA of two normal dogs, there was significantly less fibrosis in normal hearts as compared to HF hearts (data not shown).
Tissue Sample Preparation In the animals undergoing high density mapping, immediately following the in vivo electrophysiological study, the heart was promptly excised out of the chest and immersed in ice-cold cardioplegia as previously described by us. After marking the exact orientation of the high density plaques, tissue samples were taken from the PLA and LAA regions of the left atrium and snap frozen in liquid nitrogen. Samples were saved in the exact orientation in which high density mapping had been performed. All samples were initially saved at −80° C. The oriented tissue samples were frozen in Tissue-Tek OCT (Optimal Cutting Temperature) compound at −80° C.

For paraffinization, the tissue was thawed and a quick wash given to clean off all the OCT. Using a PCF LEICA 1050 Tissue Processor, the tissue was embedded in paraffin. The tissue processor uses 10% NBF (Neutral Buffered Formalin) for fixing and the tissue dehydration is performed with incremental concentrations of Ethanol (ETOH), ETOH is exchanged with xylene and finally xylene is exchanged with paraffin at 58° C. Then tissue is embedded in a paraffin block.
Masson's Trichrome Staining.

Tissue sections were cut 4 µm apart. Paraffin was removed by placing the tissue section in histology grade xylene for two minutes and the process was repeated four times changing xylene solution after every two minutes. Finally, the xylene was washed away with ETOH for one minute in absolute ETOH, then again for one more minute with fresh absolute ETOH, followed by wash in 95% ETOH for 30 seconds, and subsequently in 70% ETOH for 45 seconds. ETOH was then washed with water for one minute. The tissue section was then ready for staining. The section was treated with Bouin's mordant at room temperature overnight. The following day the tissue section was rinsed in running water to remove excess yellow. The tissue section was stained in Weigert's Solution for 7 minutes. Next, it was dipped once in 1% acid alcohol and immediately rinsed. The section was then stained in Beibrich Scarlet-Acid fuchsin for 2 minutes, followed by a rinse in distilled water. Subsequently, the tissue section was stained in phosphomolybdicphosphotungstic acid solution for 6 minutes, followed by another rinse in distilled water. The issue section was then stained in Aniline Blue solution for 5 minutes, followed by another rinse in distilled water. Immediately, the tissue was dipped once in 1% Glacial acetic acid and quickly rinsed. The tissue section was then dehydrated in twice in each concentration of 95% and 100% of ETOH, which was later exchanged with xylene. A coverslip was finally placed on the tissue section for microscope examination.

Example 6. EGM Analysis

Custom analysis tools developed in MATLAB (Mathwork, Natick, Mass.) were used for all offline EGM analysis. The signals were divided into 4 second segments to account for any variability of the both the signals and the measurements of the signals. We have previously shown that dominant frequencies averaged from multiple 4-second segments were a better reflection of activation rates than single segments of any length. The following four measurements were computed.

Dominant Frequency (DF).

DF is a frequency domain measure of activation rate. Following band-pass filtering with cutoff frequencies of 40 and 250 Hz and rectification, the power spectrum of the EGM segment was computed using the fast Fourier transform. The frequency with the highest power in the power spectrum was considered the DF.

Organization Index (OI).

OI is a frequency domain measure of temporal organization or regularity. It has been shown that AF episodes with recordings with high OI are more easily terminated with burst pacing and defibrillation. OI was calculated as the area under 1-Hz windows of the DF peak and the next three harmonic peaks divided be the total area of the spectrum from 3 Hz up to the fifth harmonic peak.

Fractionation Interval (FI).

FI is the mean interval between deflections detected in the EGM segment. Deflections were detected if they meet the following conditions: 1) the peak-to-peak amplitude was greater than a user determined noise level, 2) the positive peak was within 10 ms of the negative peak, and 3) the deflection was not within 50 ms of another deflection. The noise level was determined by selecting the amplitude level that would avoid detection of noise-related deflections in the iso-electric portions of the signal. FIs≤120 ms have been considered CFAE. The 120 ms criterion was used to calculate the % CFAE in each region for both low density and high density mapping. FI is dependent on both the AF cycle length and the fractionation of the EGM.

Shannon's Entropy (ShEn).

ShEn is a statistical measure of complexity. The 4000 or 3908 (depending on the 1 kHz or 977 Hz sample rate) amplitude values of each EGM segment were binned into one of 29 bins with width of 0.125 standard deviations. ShEn was then calculated in accordance for equation (1).

$$ShEn = \frac{-\sum_{i=1}^{29} p_i \log_{10} p_i}{\log_{10} p_i} \quad (1)$$

In this equation, $p_i$ is the probability of an amplitude value occurring in bin i. The above measures were assessed for each pixel/electrode on each plaque. There was a small number of electrodes (<10%) where signal (EGM) quality was inadequate (for example, due to noise, poor contact) for assessment of the above measures. These pixels are shown as grey in FIGS. 8 and 9.

Example 7. Tissue Analysis

Tissue sections were examined at 4× magnification (bright-field). Each slide was divided into 48 to 110 microscopic fields, depending on the size of the section (see FIG. 3B, as well as FIGS. 8 and 9; the figures show examples of how each slide (section) was divided into multiple component microscopic fields). Digital pictures of these fields were taken. Digital images were manually edited to remove all tissue elements that could not be classified as myocardium, fibrosis, or fat (for example, blood vessels, nerves, etc.). A custom MATLAB program was used to semi-automatically classify all pixels in the edited images. In each 4× tissue section, myocardium (red), fibrosis (blue) and fat (white) were classified based on the pixels' RGB values. The percentage breakdown of fibrosis vs. myocardium vs. fat was then calculated for each 4× tissue section. Mean percentage of fibrosis vs. myocardium vs. fat for an entire PLA or LAA section was taken as the mean of all respective percentages for each individual 4× section. Heterogeneity of fat vs. myocardium vs. fibrosis for a PLA or LAA was calculated as the standard deviation (SD) of the pixel counts of all the individual 4× sections that comprised that PLA or LAA.

Example 8. Tissue and EGM Correlation

Each tissue section was divided into 4 quadrants. The high-density recordings, after being aligned to underlying tissue orientation, were also divided into 4 quadrants (see schematic in FIG. 3B). In each quadrant, the absolute amount of fat, fibrosis, and myocardium was assessed. Linear regression analysis was performed to assess the correlation between tissue and EGM characteristics.

Example 9. Statistical Methods

All data are reported as mean±SE. Mixed effects ANOVA was used to compare the mean DF, OI, FI, and ShEn between HF and normal dogs and among pulmonary vein (PV), PLA, and LAA. SDs to quantify spatial heterogeneity were also analyzed in a similar fashion. In the HF dogs that underwent high-density mapping, comparison of EGMs between the PLA and LAA were made using unpaired t tests (as these regions were mapped at separate times during the electrophysiological study [that is, not simultaneously as was the case with low-density mapping]). Comparisons of tissue characteristics between the PLA and LAA were made using paired t tests. Before and after comparisons made in the same animals (for example, before and after double autonomic blockade) were assessed for significant differences via paired t tests.

Tissue and EGM correlations were performed by dividing each tissue section into 4 quadrants paired with the EGM characteristics (DF, OI, FI, and ShEn) of the high-density maps similarly divided into 4 quadrants and performing linear regression analysis. P≤0.05 was taken as significant for all the above analyses.

Example 10. Results

AF EGMs in HF Versus Normal Left Atrium
Dominant Frequency

Mixed effect ANOVA showed significantly lower mean DFs with HF than in normals (P=0.0002), but no significant difference in mean DF between sites (P=0.65; FIG. 4A). Heterogeneity (SD) of DF was also lower in HF than in normals, but with significant regional differences (that is, dispersion) within the left atrium (P=0.0007; FIG. 4B). SD of DF for normals was significantly higher in PV than in the PLA and LAA (P<0.01), whereas SD of DF of the PV and PLA were significantly higher than the LAA with HF (P<0.02).

Organization Index

Mean OI was significantly higher in HF dogs than in normals (P=0.0001), with significant regional differences within the left atrium (P=0.0002; FIG. 4C). For normal dogs, the OIs were lower in the PLA than in the LAA (P<0.03). For HF dogs, the OIs were lower in the PV and PLA than in the LAA (P<0.04). SD of OI was not different between HF and normals (P=0.59) but showed regional differences within the left atrium (FIG. 4D). SD of OI was significantly higher in the PLA than in the LAA (P<0.002).

Fractionation Interval

Mean FI was significantly higher in HF dogs than in normals (P<0.0001), with significant regional differences within the left atrium (P=0.003; FIG. 4E). For normal dogs, the FIs were significantly lower in the PV and PLA than in the LAA (P<0.03). SD of OI was significantly lower in the HF dogs than in the normal dogs (P<0.0001) but showed no significant regional differences within the left atrium (FIG. 4F).

Percentage of CFAEs

Percentage CFAE was significantly lower in HF than in normals in the PV (72±4 versus 88±4%; P=0.002), PLA (59±4 versus 92±2%; P<0.001), and LAA (59±5 versus 80±6%; P=0.003). In HF, % CFAE was significantly greater in the PV than in the PLA or LAA (P<0.05, for both comparisons). In normals, % CFAEs were significantly greater in the PLA and PV than in the LAA (P<0.05, for both comparisons).

Shannon Entropy

Mean ShEn trended lower in HF dogs than in normals (P<0.08), with significant regional differences within the left atrium (P=0.003; FIG. 4G). For HF dogs, ShEn levels were significantly higher in the PV and PLA than that in the LAA (P<0.0006). SD of ShEn was not different between HF dogs and normal dogs (P=0.14) or between sites (P=0.31; FIG. 4H).

AF EGM Characteristics in the HF PLA Versus LAA (With High-Density Plaques)

In both the PLA and LAA, there was no difference in DF between low- and high-density plaques (data not shown). However, OI was lower, FI was greater, and ShEn was lower with high-density plaques compared with the low-density plaques (data not shown). This is likely because of the difference in inter-electrode distance between the plaques; increasing inter-electrode distance for the same set of bipolar recordings results in a decrease in OI, decrease in FI, and increase in ShEn (data not shown). All the remaining AF mapping data below was obtained with high-density plaques. In the 1 dog that underwent both low- and high-density mapping, the differences between low- and high-density mapping were consistent with the overall mean differences for all dogs between low-versus high-density mapping (data not shown).

Overall, differences between the PLA and LAA during high-density mapping (where the PLA and LAA were mapped sequentially) were similar to those found during low-density mapping (where the PV, PLA, and LAA were mapped simultaneously). OI was significantly lower in the HF PLA compared with the LAA, with ShEn trending toward being greater in the PLA than in the LAA (FIG. 5A). DF, OI, FI, and ShEn were all more heterogeneous in the HF PLA than the LAA (FIG. 5B).

Distribution of Fibrosis, Fat, and Nerves in the HF Left Atrium

The PLA had significantly more fat than the LAA (36.4±2.8% versus 21.6±2.2%; P<0.001) (FIG. 6A, subpanel i.). Percentage myocardium was greater in the LAA than in the PLA (53.5±2.4% versus 35.6%±2.9%; P<0.001). There was no significant difference in fibrosis between the PLA and LAA.

Percentage fat was assessed in the PLA in a small number of normal dogs (n=3) and was found to be no different than in HF (36.4±2.8% versus 30.1±2.1%; P=0.22).

Myocardium and fibrosis were more heterogeneously distributed in the PLA than in the LAA (SD of % myocardium in PLA versus LAA=20.5±1.7% versus 14.1±1.3%; P=0.01; SD of % fibrosis in PLA versus LAA=16.9±1.9% versus 12.3±1.5%; P=0.02; FIG. 6A, subpanel ii.). Fat also trended toward being more heterogeneous in the PLA than in the LAA (17.3±1.7% versus 12.3±2.3%; P=0.07).

FIG. 6B shows examples of significantly greater fat in the PLA (subpanels i. and iii.) than the LAA (subpanels ii. and iv.). These panels also demonstrate that fat, fibrosis, and myocardium were more heterogeneously distributed in the PLA than in the LAA. A significant number of nerve trunks were noted in the PLA fat (43±9; FIG. 6B, subpanel i., and FIG. 9C for examples of nerve trunks/bundles in the PLA). In contrast, no nerve trunks were found in the LAA.

Correlation Between AF EGM Characteristics and Fibrosis

DF was negatively correlated to % fibrosis (r=−0.45; P=0.006; FIG. 7A, subpanel i.), whereas FI was positively correlated with % fibrosis (r=0.42; P=0.01; FIG. 7A, subpanel ii.) in the PLA. Heterogeneity (SD) of DF and heterogeneity (SD) of FI were correlated with heterogeneity (SD) of fibrosis (for DF, r=0.41; P=0.01; for FI, r=0.47; P=0.004; FIG. 7B, subpanels i. and ii., respectively).

FIG. 8A shows an example of OI being lower and more heterogeneous (that is, greater SD) in the HF PLA than the LAA. FIG. 8B shows an example of DF being more heterogeneous in the HF PLA compared with the LAA. Subpanels i. and ii. in each panel show the Masson-Trichrome stained PLA and LAA, respectively. Subpanels iii. and iv. in FIG. 8A show the corresponding OI maps for each region mapped. Similarly, subpanels iii. and iv. in FIG. 8B show the corresponding DF maps for each region mapped.

Effect of Double Autonomic Blockade on EGM Content in the HF Left Atrium

In the PLA, double autonomic blockade lead to a significant decrease in DF (from 6.8±0.6 to 6.1±0.7 Hz; P<0.001) and an increase in FI (from 138±18 to 158±26 ms; P=0.002; FIG. 9A). The increase in FI by double autonomic blockade was paralleled by a decrease in % CFAEs in the PLA (from 34±15% to 21±13%; P=0.01). A trend toward the decrease of ShEn was noted in PLA in the presence of double autonomic blockade (from 0.76±0.01 to 0.73±0.01; P=0.098). No change in OI was noted in the PLA with double autonomic blockade. In the LAA, there was no change in any of these measures in the presence of double autonomic blockade (FIG. 9A).

FIG. 9B shows examples of EGMs before and after autonomic blockade; as shown, the AF EGMs become significantly slower and less fractionated after autonomic blockade. FIG. 9C shows that with autonomic blockade, DF changes significantly over regions of fat in the PLA. In FIG.

9C, subpanel i. shows the PLA being mapped. Subpanels ii. and iii. show the DF map before and after autonomic blockade; as shown, there is a significant decrease in DF after autonomic blockade. Moreover, the decrease in DF is most pronounced over regions of fat that contain large nerve trunks (encircled regions). Subpanel iv. highlights a large nerve trunk seen in subpanel i. In the PLA, change in ShEn (ΔShEn) with autonomic blockade was positively correlated with % fatty tissue (r=0.42; P<0.05; FIG. 7C).

To the extent that the present application references a number of documents, those references are hereby incorporated by reference herein in their entirety.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

The invention claimed is:

1. A method of targeting autonomic nerve for ablation in a subject, comprising:
    (a) performing at least one electrogram (EGM) analysis of a plurality of recorded atrial electrograms (EGMs) for a tissue in a region suspected of having autonomic nerve tissue;
    (b) assessing the plurality of EGMs before or after autonomic blockade; and
    (c) determining a first outcome of executing step (b) and a second outcome of executing step (b) for a region based upon the one or more significant changes in EGM characteristics with autonomic blockade;
wherein the first outcome triggers a first decision to avoid ablation of the analysis region and the second outcome triggers a second decision to perform ablation of the analysis region of the tissue.

2. The method of claim 1, wherein step (a) comprises at least one analytical subroutine selected from the group consisting of dominant frequency analysis (DF), organizational index analysis (OI), fractional interval analysis (FI) and Shannon Entropy analysis (ShEn).

3. The method of claim 1, wherein the first outcome consists of no significant changes in EGM characteristics with autonomic blockade and the second outcome consists of at least one significant change in EGM characteristics with autonomic blockade.

4. The method of claim 1, wherein step (b) is performed with one or more analytical subroutines comprising at least one member selected from the group consisting of DF, OI, FI and ShEn.

5. The method of claim 1, wherein the tissue comprises posterior left atrium (PLA) before, during or after double autonomic blockade.

6. The method of claim 1, further comprising acquiring the plurality of recorded atrial EGMs for a tissue in a region suspected of having autonomic nerves in real-time from a subject.

7. A computer program product, comprising a non-transitory tangible computer readable medium having computer readable program code for targeting autonomic nerve for ablation in a subject, wherein the targeting autonomic nerve for ablation comprises:
    (a) performing at least one electrogram (EGM) analysis of a plurality of recorded atrial electrograms (EGMs) for a tissue; and
    (b) executing the following instructions:
        (i) assessing the plurality of EGMs before or after autonomic blockade; and
        (ii) determining a first outcome of executing step (i) and a second outcome of executing step (i) for a region based upon the one or more significant changes in EGM characteristics with autonomic blockade;
    wherein the first outcome triggers a first decision to avoid ablation of the analysis region and the second outcome triggers a second decision to perform ablation of the analysis region of the tissue.

8. The computer program product of claim 7, wherein step (a) comprises at least one analytical subroutine selected from the group consisting of dominant frequency analysis (DF), organizational index analysis (OI), fractional interval analysis (FI) and Shannon Entropy analysis (ShEn).

9. The computer program product of claim 7, wherein for targeting autonomic nerve for ablation comprises assessing EGM's from posterior left atrium (PLA) before, during or after double autonomic blockade.

10. The computer program product of claim 7, further configured to acquire the plurality of recorded atrial EGMs for a tissue in a region suspected of having fibrosis or autonomic nerves in real-time from a subject.

11. A kit comprising:
    (a) a computer program product of claim 7; and
    (b) instructions.

* * * * *